US00PP14245P39

(12) United States Plant Patent
Zary

(10) Patent No.: US PP14,245 P3
(45) Date of Patent: Oct. 21, 2003

(54) FLORIBUNDA ROSE PLANT NAMED 'JACZIBWO'

(50) Latin Name: *Rosa hybrida*
Varietal Denomination: JACZIBWO

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/000,260

(22) Filed: Nov. 30, 2001

(65) Prior Publication Data

US 2003/0106121 P1 Jun. 5, 2003

(51) Int. Cl.[7] ..... A01H 5/00

(52) U.S. Cl. ..... Plt./150

(58) Field of Search ..... Plt./150

(56) References Cited

U.S. PATENT DOCUMENTS

PP4,844 P * 5/1982 Tantau ..... Plt./150

* cited by examiner

*Primary Examiner*—Bruce R. Campell
*Assistant Examiner*—W C Haas
(74) *Attorney, Agent, or Firm*—Klarquist Sparkman, LLP

(57) ABSTRACT

Floribunda rose plant having large showy clusters of bright red flowers; free flowering with rapid repeat bloom; dark green, healthy foliage resistant to rust, powdery midlew and blackspot; and vigorous, upright branching growth.

1 Drawing Sheet

Genus and species: *Rosa hybrida.*
Variation denomination: 'Jaczibwo'.

SUMMARY OF THE INVENTION

The present invention relates to a new and distinct variety of rose plant of the floribunda class which was originated by me by crossing the variety 'Showbiz' (U.S. Plant Pat. No. 4,844) with an unnamed seedling (unpatented).

BACKGROUND OF THE INVENTION

The primary objective of this breeding was to produce a new rose variety having the bright red flower color, vigorous groth and healthy foliage of the male parent combined with the large flower truss and free flowering habit of the female parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Large showy flower clusters;
2. Bright red flower color;
3. Free flowering with rapid repeat bloom;
4. Dark green, healthy foliage resistant to rust, powdery mildew and blackspot; and
5. Vigorous, upright, branching growth.

Asexual reproduction of this new variety by budding on Dr. Huey rootstock, as performed at Wasco, Calif., shows that the foregoing and all other characteristics and distinctions come true to form and are established and transmitted through succeeding propagations.

COMPARISON WITH PARENTS

Larger plant than 'Showbiz' with larger foliage. More flowers than the unnamed red floribunda seedling with faster rebloom.

COMPARISON WITH SIMILAR VARIETY

More bloom, excellent repeat bloom and more vigorous than other red floribundas presently on the market that are known to the inventor.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'Showbiz' (U.S. Plant Pat. No. 4,844).
*Pollen parent.*—Unnamed seedling (unpatented) ('Tournament of Roses'×'Espirit').

FLOWER

Observations made from plants of two years of age grown in a garden environment at Somis, Calif., January, 2000–May, 2001.

Blooming habit: Continuous.

Bud:

*Size.*—About 22–24 mm long and 15–18 mm in diameter when the petals start to unfurl.

*Form.*—The bud form is pointed ovoid.

*Color.*—When sepals first divide, bud color is Red Group 46A. When half blown, the upper sides of the petals are Red Group 45A; and the lower sides of the petals are Red Group 45A.

*Sepals.*—Color: Upper surface: Yellow-Green Group 144A with Red-Purple Group 59B in the center. Lower surface: Yellow-Green Group 144B. Length: 20–26 mm. Width: 6–8 mm. Shape: Subulate. Surface texture: Upper surface: Smooth. Lower surface: Canescent. There are three normally appendaged sepals. There are two unappendaged sepals with glandular edges.

*Receptacle.*—Color: Yellow-Green Group 144A. Shape: Funnel. Size: Medium, about 7 mm×7 mm. Surface: Smooth, glandular with few glands at bottom.

*Peduncle.*—Length: Medium, averaging about 45–85 mm. Surface: Glandular. Color: Yellow-Green Group 146D with anthocyanin of Red-Purple Group 60A. Strength: Stiff, erect.

Bloom:

*Size.*—Medium. Average open size is 65–70 mm.

*Borne.*—In flat clusters of 4–7 blooms.

*Stems.*—Strength: Strong. Average length is about 15–25 cm.

*Form.*—When first open: Bloom is flat with a loose open form. Permanence: Retains its form to the end.

*Petalage.*—Number of petals under normal conditions: 15–20.

*Color.*—The upper sides of the petals are Red Group 45A. The reverse sides of the petals are Red Group 53B. The base of each petal is Red Group 55C. The major color on the upper side is Red Group 45A.

*Variegations.*—None.

*Discoloration.*—The general tonality at the end of the first day: Red Group 45A. At the end of the third day: Red Group 45A. By day seven, the outer color of the petals changes to Red-Purple Group 63A.

*Fragrance.*—None.

Petals:

*Texture.*—Thin, leathery.

*Shape.*—Round.

*Margin.*—Entire.

*Apex shape.*—Mucronate.

*Base shape.*—Obtuse.

*Form.*—Tips slightly recurved.

*Arrangement.*—Informal. Petaloids in the center are few (2–3). Petaloid Color: Red Group 45A with prominent vein of Yellow-White Group 158D.

*Persistence.*—Petals drop off cleanly before drying.

*Lastingness.*—On the plant: Long (about 8–9 days). As a cut flower: Not tested.

Reproductive parts:

*Stamens.*—Number: 130–150. Length: 8–11 mm. Anthers: Length: 2–3 mm. Color: Yellow-Orange Group 20C. Arrangement: Regular around styles. Filaments: Color: Red Group 53D. Length: 6–8 mm. Pollen: Color: Yellow-Orange Group 21D.

*Pistils.*—Number: 60–80. Styles: Color: Greyed-Green Group 196C. Length: 4–6 mm. Stigmas: Color: Yellow-Orange Group 22C. Length: 1–1.5 mm.

*Hips.*—None observed.

PLANT

*Form.*—Shrub.

*Growth.*—Very vigorous, upright and branching.

*Mature plant.*—Height: 1 meter. Width: 0.75 meters.

Foliage: Number of leaflets on normal mid-stem leaves: 5–7.

*Size.*—Length: 12–14 cm. Width: 7–9 cm.

*Quantity.*—Normal.

*Color.*—New foliage: Upper side: Greyed-Purple Group 183A with undertones of Green Group 141C. Lower side: Greyed-Purple Group 184 B. Old foliage: Upper side: Green Group 137B. Lower side: Yellow-Green Group 146A with Red Group 53D on margins.

Leaflets:

*Size.*—Medium (4.5 cm long×3 cm wide).

*Shape.*—Elliptic.

*Base shape.*—Obtuse.

*Apex shape.*—Mucronate.

*Texture.*—Glossy, smooth.

*Edge.*—Serrated.

*Serrations.*—Single, large.

*Petiole color.*—Upper: Green Group 143C with prominent Red Group 53C. Lower: Yellow-Green Group 145B.

*Petiole rachis.*—Color: Green group 143A. Underside: Smooth.

*Stipules.*—Inner surface color: Yellow-Green Group 144A; Outer surface color: Yellow-Green Group 145B. Size: Medium, serrated (about 22 mm.)

*Disease resistance.*—Resistant to mildew, blackspot and rust under normal growing conditions.

*Pest resistance.*—Not tested.

Wood:

*New wood.*—Color: Greyed-Purple Group 184B. Bark: Smooth.

*Old wood.*—Color: Yellow-Green Group 144B. Bark: Smooth.

Prickles (thorns):

*Quantity.*—On main canes from base: 16–18 per 15 cm of stem length. On laterals from main canes: 16–18 per 15 cm of stem length.

*Form.*—Hooked slightly downward.

*Length.*—10–12 mm.

*Color when young.*—Greyed-Purple Group 185B.

*Color when mature.*—Greyed-Purple Group 182A.

Small prickles:

*Quantity.*—On main stalks: None. On laterals: None.

Winter hardiness: Hardy to Zone 5.

I claim:

1. A new and distinct variety of rose plant of the floribunda class, substantially as herein shown and described, characterized particularly by large, showy clusters of bright red flowers; free flowering with rapid repeat bloom; dark green, healthy foliage resistant to rust, powdery mildew and blackspot; and vigorous, upright, branching growth.

* * * * *

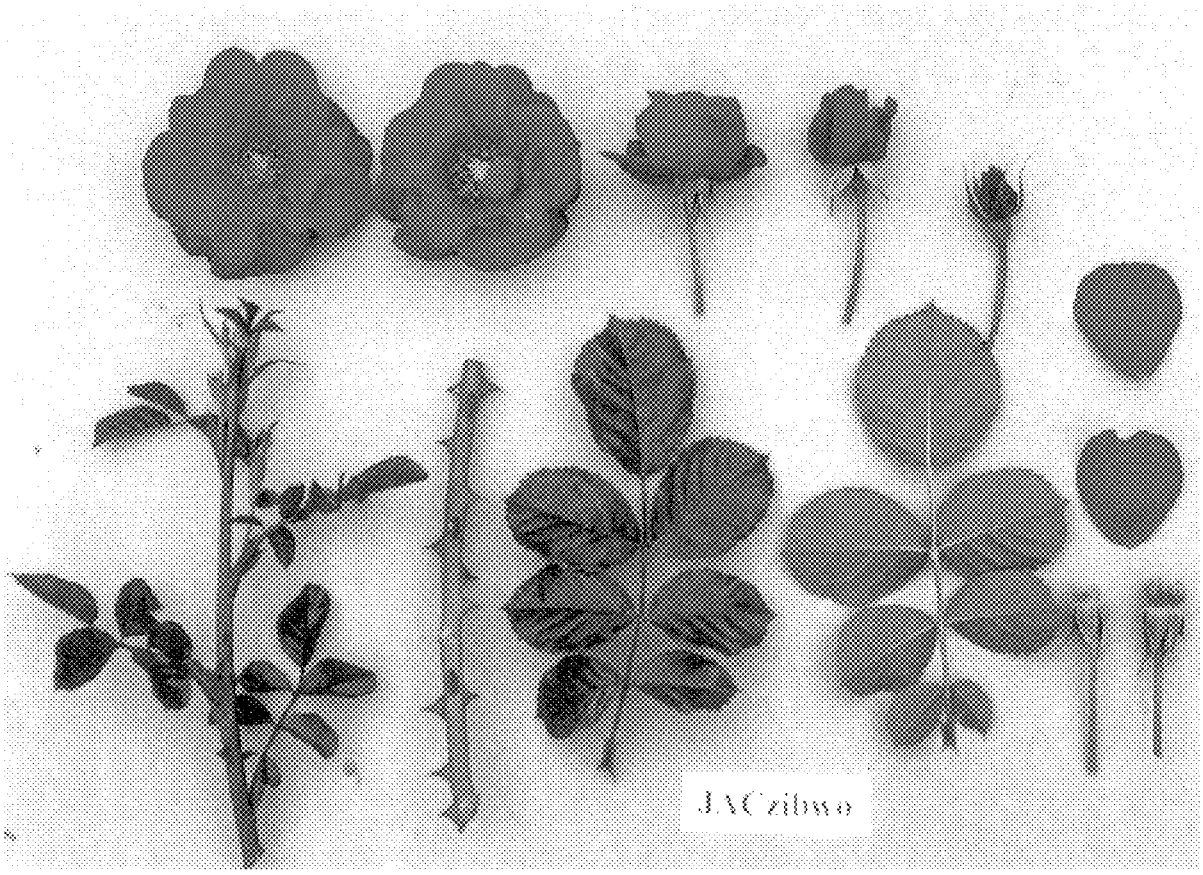
J.A.Czibwo